United States Patent [19]

Adigamov et al.

[11] 4,232,176
[45] Nov. 4, 1980

[54] METHOD OF REMOVING ALUMINUM-CONTAINING CATALYST FROM PHENOL ALKYLATION PRODUCTS

[76] Inventors: Engel R. Adigamov, Revoljutsionnaya ulitsa, 11, kv. 31, Bashkirskaya ASSR, Sterlitamak; Yakov A. Gurvich, Sretensky bulvar, 6, kv. 61, Moscow; Alexandr G. Liakumovich, ulitsa Galeeva, 10, kv. 8, Kazan; Igor J. Logutov, ulitsa Druzhby, 47, kv. 50, Bashkirskaya ASSR, Sterlitamak; Jury I. Michurov, prospekt Lenina, 13, kv. 4, Bashkirskaya ASSR, Sterlitamak; Alexei S. Polenov, prospekt Oktyabrya, 15, kv. 16, Bashkirskaya ASSR, Sterlitamak; Vladimir A. Yanshevsky, Kommunisticheskaya ulitsa, 42, kv. 12, Novokuibyshevsk, all of U.S.S.R.

[21] Appl. No.: 695,753

[22] Filed: Jun. 14, 1976

[51] Int. Cl.$^3$ .................... C07C 37/70; C07C 37/84
[52] U.S. Cl. .................................. 568/756; 568/789; 568/794

[58] Field of Search ........... 260/624 C, 624 R, 624 A, 260/621 A

[56] References Cited

U.S. PATENT DOCUMENTS

| | | | |
|---|---|---|---|
| 2,831,898 | 4/1958 | Eckes et al. | 260/624 C |
| 3,652,685 | 3/1972 | Geddes | 260/624 C |
| 3,766,276 | 10/1973 | Goddard | 260/624 R |
| 3,970,708 | 7/1976 | Katsumoto | 260/624 C |

*Primary Examiner*—Werren B. Lone
*Attorney, Agent, or Firm*—Haseltine, Lake & Waters

[57] ABSTRACT

Method of removing aluminum-containing catalyst from phenol alkylation products comprises treating phenol alkylation products with water at a temperature of 165°–250° C., with water being in molar excess to aluminum in a range of 3–20. The resulting residue of meta-aluminate is easily separated by filtration.

The present invention allows eliminating constant control of aluminum content in alkylation products, easily removing the catalyst therefrom and eliminating the loss of phenol alkylation products.

3 Claims, No Drawings

METHOD OF REMOVING ALUMINUM-CONTAINING CATALYST FROM PHENOL ALKYLATION PRODUCTS

The present invention relates to the field of petrochemical synthesis pertaining to the alkylation processes of phenol and its homologues in the presence of an aluminum-containing catalyst, and more particularly, it relates to methods of removing aluminum-containing catalyst from the products of alkylation of phenol and homologues thereof.

Alkylation processes of phenol and its homologues in the presence of catalysts, being aluminum solutions in phenols, are widely used in the art.

Alkylation products, for removing individual alkylphenols therefrom, are rectified at a temperature of 130°–250° C. The admixtures of the aluminum-containing catalyst should be removed from said products before rectification, since aluminium promotes secondary reactions, e.g. isomerization. The removal of said catalyst is carried out by the destruction thereof.

The catalyst can be destroyed by water with the formation of aluminum hydroxide which is then separated as a solid residue by means of filtration or centrifuging. The catalyst decomposition reaction can be presented as the following scheme:

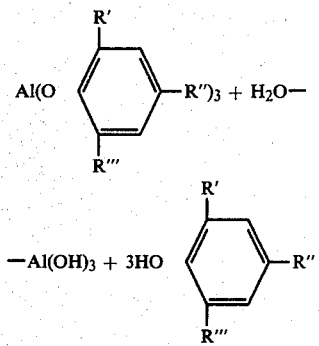

where R', R" and R''' are alkyl or hydrogen.

Aluminum hydroxide precipitates as a gel which is difficult to filter showing a low rate and requiring large filtration surfaces.

The catalyst can also be decomposed by using a dilute acid. Aluminum passes into the acidic layer as a salt and it is separated from alkylation products by settling. However, in this case phenolic waste water is formed and it requires expensive treatment. Besides, careful washing of alkylation products with water is required because even small quantities of acid promote secondary reactions. The quantity of phenolic waste water is several times higher than that of the acid solution used.

In spite of all the problems, the destruction of aluminum-containing catalyst with water, being the cheapest reagent, is the most economical process, therefore an improvement of this method has been proposed (FRG Patent No. 1,199,277, Apr. 17, 1963).

The essence of the method according to said Patent resides in the following.

Approximately 1–6 moles of water (preferably 3–6 moles) per mole of aluminum are added to alkylation products containing aluminum solution in phenol as a catalyst. Water treatment is carried out during 15 minutes at a temperature of 140° C.

Thus a suspension is formed which is filtered. According to said Patent, for better separating the residue and increasing filtration rate, it is suggested to introduce solvents into the reaction mixture (olefins, aromatic hydrocarbons, nitrobenzene, monochlorotoluene, petroleum ether, etc.), which reduce the solution viscosity and decrease the residue solubility.

The above-described method has certain disadvantages. 1. A very exact proportioning of water in the reaction mixture is required (3–6 moles per mole of Al). Exact proportioning is difficult to attain because in an industrial process aluminum content in alkylation products varies in a wide range (1.5–2 times) due to concentration fluctuations thereof in the starting phenols and decomposition thereof in the alkylation process due to small quantities of water introduced with the starting materials (phenols, olefins). 2. The resulting residue contains combined organic compounds, which leads to unrecoverable losses of phenols. 3. Though the addition of an inert solvent improves suspension separation, it results in additional power consumption for the solvent recovery. 4. $Al(OH)_3$, obtained as a residue, is fine granular, it clogs the filter surface and is therefore difficult to filter.

The object of the present invention is to improve the method of removing aluminum-containing catalyst from phenol alkylation products by destroying it with water in order to increase the process productivity and to eliminate losses of phenols and alkylation products thereof.

Said object has been accomplished by the provision of a method of removing aluminum-containing catalyst from phenol alkylation products by water treatment thereof at an elevated temperature, followed by separating the resultant residue, in which, according to the invention, water treatment of phenol alkylation products is carried out at a temperature of 165°–250° C. until crystalline meta-aluminate is formed.

The process is run most effectively at a temperature range of 185°–220° C.

The quantity of water required for treatment can be varied in a wide range, it may either correspond to the stoichiometric quantity or exceed it and be in the range of 3–20 moles per mole of aluminum, however, a water excess of 4–10 moles is preferable.

An excess quantity of water allows carrying out the process continuously, without recourse to constant control of aluminium content in the alkylate, thus simplifying the process technology.

In the above-specified temperature range, namely, 165°–250° C., a solid residue is formed being a coarse-crystalline meta-aluminate, insoluble in a hydrocarbon medium and which can be easily separated by any known method, e.g. by filtration. Alkylphenols adsorbed on the surface of the residue are easily separated therefrom by treating it with a solvent that is inert to it but dissolves alkylphenols well.

Paraffin, olefin, naphthene hydrocarbons, halogen derivatives thereof, alcohols, esters, ketones, nitro compounds, etc. are used as such solvents.

The main advantage of the invention is the formation of coarse-crystalline meta-aluminate residue (HOAlO). Such a residue is easily filtered and does not contain combned alkylphenols.

Water treatment at a temperature lower than 165° C. does not ensure the formation of meta-aluminate, and water treatment at a temperature higher than 250° C. is disadvantageous because the end product is unstable.

The herein-proposed method of removing aluminum-containing catalyst from phenol alkylation products can be realized with any version of the alkylation process (either continuous or intermittent).

For a better understanding of the invention several specific examples are presented hereinbelow.

EXAMPLE 1

3 grams of metallic aluminum are dissolved in 300 grams of phenol during 1 hour at a temperature of 160°–180° C. Then the aluminum solution in phenol is cooled down to 100° C. and isobutylene is passed through it during 6 hours.

The alkylate content in mol.% is: phenol, 9%; 2-tert-butylphenol, 13%; 2,6-ditertbutylphenol, 68%; 2,4;1-ditertbutylphenol, 3%; 2,4,6-terbutylphenol, 7%.

8 ml of water are added to the resultant mixture (mol. ration of $H_2O$: Al being 4:1), mixed during 15 minutes, then the mixture is heated to 165° C. and kept at this temperature with simultaneous vacuum distillation of water during 2 hours.

The resultant suspension is filtered under nitrogen pressure of 5 atm (gauge) through a filter with the working operating surface area of 7 cm$^2$,$\phi$ of pores<250$\mu$.

Filtration time is 25 minutes. The residue is a coarse crystalline meta-aluminate, $\phi$ of particles >200$\mu$.

A small amount of alkylphenols adsorbed on the residue surface is removed by using hexane as a solvent.

EXAMPLE 2

Alkylation products are obtained as in Example 1. After terminating the isobutylene supply, 40 ml of water are added to the reaction products (mol. ratio of $H_2O$:Al=20:1) and mixed during 15 minutes. Then the mixture is heated to 185° C., kept at this temperature during 30 minutes till the formation of meta-aluminate with simultaneous water distillation, and filtered as described in Example 1. Filtration time is 22 minutes.

EXAMPLE 3

3 grams of aluminum are dissolved in 300 grams of dicresolic fraction at a temperature of 180°–190° C. during 1 hour. Then the solution is cooled down to 100° C. and isobutylene is passed during 6 hours. 20 ml of water are added to the resultant alkylate (mol. ratio of $H_2O$:Al=10:1) and mixed during 15 minutes. The mixture is heated to 250° C. with simultaneous water distillation, and filtered immediately as in Example 1.

Filtration time is 20 minutes. The alkylation products obtained according to Examples 1,2,3 were analyzed for Al content therein and the residue was studied.

In the IR-spectrum of the heated residue obtained in Examples 1,2,3 there is a strong absorption band at 1076 cm$^{-1}$, characteristic of meta-aluminate. Differential thermal analysis data also indicate phase transition taking place upon heating of the residue.

Photocalorimetric analysis of the filtrate for aluminum content after filtration showed complete absence of Al in it. Alkylphenols contained in the filtrate display complete stability under prolonged heating (2–4 hours) to 250° C., which proves the absence of Al in the alkylate, since it is known that the presence of even traces of Al in the alkylate results in dealkylation processes under such conditions. The composition of alkylphenols after removing the catalyst therefrom by the method of the invention, is identical to the initial one.

The present method of removing the catalyst is also applicable t alkylation products forming when phenols are alkylated with other olefins, e.g. ethylene, propylene, isoamylenes, etc.

What we claim is:

1. A method of removing aluminum-containing catalyst from phenol alkylation products, which consists essentially of treating said alkylation products with water at a temperature of 185°–200° C. till crystalline meta-aluminate is formed, and separating the resultant meta-aluminate.

2. The method according to claim 1, wherein the water treatment is carried out with an excess molar ratio of water to Al being 3–20.

3. The method according to claim 1, wherein the meta-aluminate residue is removed by filtration and is washed with a solvent inert thereto.

* * * * *